(12) United States Patent
Crandall

(10) Patent No.: US 6,316,428 B1
(45) Date of Patent: *Nov. 13, 2001

(54) TOPICAL MOISTURIZING COMPOSITION AND METHOD

(76) Inventor: Wilson Trafton Crandall, Rte. 616 Jolly Hill, Ft. Defiance, VA (US) 24437

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/383,779

(22) Filed: Aug. 26, 1999

Related U.S. Application Data

(63) Continuation of application No. 08/876,764, filed on Jun. 16, 1997, now Pat. No. 5,945,409, which is a continuation-in-part of application No. 08/403,241, filed on Mar. 10, 1995, now Pat. No. 5,639,740.

(51) Int. Cl.[7] ............... A61K 31/685; A61K 31/23
(52) U.S. Cl. ............... 514/78; 514/159; 514/552; 514/847; 514/861; 514/936; 514/937; 514/944
(58) Field of Search .................. 514/78, 179, 552, 514/847, 861, 936, 937, 944

(56) References Cited

U.S. PATENT DOCUMENTS

| | | | |
|---|---|---|---|
| 3,062,721 | 11/1962 | Grate | 424/658 |
| 3,952,099 | 4/1976 | Smith | 514/152 |
| 3,957,971 | 5/1976 | Oleniacz | 424/450 |
| 4,701,471 | 10/1987 | Loucks, Sr. et al. | 514/784 |
| 4,760,096 | 7/1988 | Sakai et al. | 514/786 |
| 4,783,450 | 11/1988 | Fawzi et al. | 514/78 |
| 4,981,681 | 1/1991 | Tosti | 424/78 |
| 5,238,933 | 8/1993 | Catz et al. | 514/236.2 |

OTHER PUBLICATIONS

Elias et al., *The Journal of Investigative Dermatology*, vol. 73, pp. 339–348 (1979).

Luisi et al., *Colloid & Polymer Science*, vol. 268, pp. 356–374 (1990).

Scartazzini et al., *Journal of Physical Chemistry*, vol. 92, pp. 829–833 (1988).

Schmolka, *Journal of Biomedical Material Research*, vol. 6, pp. 571–582 (1972).

Williman et al., *Journal of Pharmaceutical Sciences*, vol. 81 (9), pp. 871–874 (1992).

*Merck Index*, (9th Edition), p. 711 (1976).

*Primary Examiner*—Shelley A. Dodson
(74) *Attorney, Agent, or Firm*—Kilpatrick Stockton LLP

(57) ABSTRACT

The present invention comprises methods and compositions for topically treating and moisturizing keratinous structures of humans and animals including skin, hair, fingernails, toenails, hooves, and horns.

23 Claims, No Drawings

TOPICAL MOISTURIZING COMPOSITION AND METHOD

PRIOR RELATED APPLICATIONS

The present application is a continuation of U.S. application Ser. No. 08/876,764, filed Jun. 16, 1997 now U.S. Pat. No. 5,945,409 which is a continuation-in-part of U.S. application Ser. No. 08/403,241, filed Mar. 10, 1995, now U.S. Pat. No. 5,639,740 which is incorporated herein by reference in its entirety.

TECHNICAL FIELD

The present invention is related to a process and composition for moisturizing and rejuvenating keratinous tissues including skin, hair, fingernails, and toenails of humans and animals, and also hooves and horns of animals. More particularly, the present invention relates to topically applying the composition disclosed herein in order to treat the affected keratinous tissue.

BACKGROUND OF THE INVENTION

The skin is the largest organ in the body and serves several important functions that are essential to life. The skin retards dehydration and also acts as a barrier to the invasion of various pathogens and noxious substances. Skin is composed of the epidermis, or upper layer, and the subjacent dermis. The epidermis is the superficial layer and gives rise to the nails, hair, sebaceous glands, sweat glands, and the parenchyma of mammary glands. The epidermis is composed of several layers. As cells from the deeper layer, the stratum germinativum, move toward the surface, they begin to synthesize the intracellular protein keratin. During subsequent movement, these cells lose their distinct nuclei and form the outermost layer of the epidermis known as the stratum corneum which is comprised of several layers of cornified epidermal cells that are embedded in an intercellular matrix of semi-polar and polar lipids. This layer acts as a transport route for various drugs, such as hydrocortisone, and also acts as a barrier to the transport of other drugs and cosmetics (Elias et al., *Journal of Investigative Dermatology* 73: 339–348, 1979). In addition, this lipid layer of the stratum corneum assists in the retention of water. The water content of the stratum corneum has a profound influence on the appearance, flexibility, texture, and dryness of the skin, and also on the absorption of drugs and other molecules into and through the skin.

With increasing age, the skin gradually loses ceramides and water and becomes drier, less flexible and supple, more wrinkled, and scaly in appearance. One of the major objectives of the cosmetic industry is to retard the drying and wrinkling of the skin that occurs with normal aging or as the result of exposure to wind, sun, cold and chemicals. As the mean age of the population increases, more people are seeking products that will retard the effects of aging on the skin and will essentially rejuvenate the skin. Increasing the moisture content of the skin is one mechanism for achieving this objective. Furthermore, enhanced skin hydration facilitates the transport of pharmaceuticals across the epidermis to reach the underlying dermis and subjacent capillaries of the lymphatic and circulatory systems.

Another objective of the cosmetic industry is to retard the drying of the hair, fingernails and toenails, which all arise from the epidermis. In addition to enhancing the youthful appearance of an individual, increased hydration of these structures prevents the painful effects of cracked nails and itchy, scaly scalp. In animals, similar problems can occur with fingernails and toenails and also with horns and hooves which are all epidermal derivatives. For example, cracked hooves can result in lameness or in injury to the coronary band, the primary growth and nutritional source for the hoof wall. Injuries to the coronary band can cause serious permanent defects in the growth of the hoof wall.

The formation of organogels containing lecithin dissolved with isopropyl palmitate or other solvents, and water, has been described by Luisi et al., *Colloid and Polymer Science* 268: 356–374 (1990) and Scartazzini et al., *The Journal of Physical Chemistry* 92: 829–833 (1988), which are incorporated herein by reference in their entirety. Williman et al., *Journal of Pharmaceutical Sciences* 81:871–874 (1992), which is incorporated herein by reference in its entirety, examined the efficacy of lecithin organogels for use in the transdermal delivery of drugs such as scopolamine and broxaterol. Williman et al., also observed that lecithin organogels had no detrimental effect on skin when compared to control samples treated with physiological saline (see page 872, column. 2, paragraph 3, *Journal of Pharmaceutical Sciences* 81:871–874 (1992)).

Catz et al., in U.S. Pat. No. 5,238,933, discloses skin permeation enhancer systems which increase the permeability of the skin to transdermally administered, pharmacologically active agents.

Smith, in U.S. Pat. No. 3,952,099, discloses dermatological compositions for enhancing the penetration of pharmacologically active agents, such compositions comprising a sugar ester in combination with a sulfoxide or phosphine oxide.

Loucks, in U.S. Pat. No. 4,701,471, discloses a cosmetic and pharmaceutical composition comprising bovine bone marrow acids mixed with lecithin for prevention of the fatty acid oxidation and odor putrefacation.

In U.S. Pat. No. 3,957,971, Oleniacz discloses moisturizing units for treating keratinous tissue comprising liposomes having a ternary lipid mixture of lecithin, dicetyl phosphate, and a sterol Sakai et al., in U.S. Pat. No. 4,760,096, discloses a skin moisturizing method and preparation containing a combination of a phosphatide such as soy lecithin, and one or more $C_{10}$–$C_{30}$ carboxylic acid sterol esters.

U.S. Pat. No. 4,783,450 to Fawzi et al. discloses the use of lecithin as a skin penetration enhancer for transdermal delivery of the drug procaterol through skin.

A method and composition for increasing the moisture of epidermal structures are needed. The composition should be easy to apply topically, enhance moisture retention, and also have the capacity to deliver compounds that will assist in moisturizing and rejuvenating keratinous structures such as the skin hair, fingernails, toenails, hooves and horns.

SUMMARY OF THE INVENTION

The present invention is a method of moisturizing keratinous tissue of a human or animal comprising the step of topically applying to the keratinous tissue of the human or animal, a composition comprising lecithin, in an organic solvent and water whereby the composition is delivered into the stratum corneum, epidermis and dermis. Another embodiment of the present invention comprises a method of treating keratinous tissue of a human or animal comprising the step of topically applying to the keratinous tissue of the human or animal, a composition comprising water dispersible lecithin.

In one embodiment, the present invention provides an easy to use therapeutic and cosmetic process for treating dry skin and for alleviating the associated irritation and cracking of the skin by topically applying the composition disclosed herein. Use of this process and composition increases the moisture content of the skin, reduces wrinkling, and provides a rejuvenated appearance to the skin. In addition, this invention has great utility for the treatment of dry and brittle fingernails and toenails, and the adjacent skin that often is dry and cracked. In another embodiment, this invention is a therapeutic and cosmetic process for application to animals with cracked and damaged horns and/or hooves. A horn or hoof dressing in show horses and cattle would produce a more vibrant and healthy appearance. In addition, rapid closure of cracks in hooves would prevent invasion by foreign material and reduce the incidence of infection.

An additional embodiment of the invention is a therapeutic and cosmetic process for the treatment of dry and thinning hair to provide increased hair growth and thickness. It is understood that the present invention also encompasses a method and composition for delivery of molecules including, but not limited, to elastin, collagen and collagen fragments, glucosamine, glucosamine sulfate, glycerol, urea, ceramides, dimethicone, N-decylmethyl sulfoxide, salicylic acid, lanolin, chondroitin sulfate, hyaluronic acid, squalene, and various alpha hydroxy compounds such as lactic acid, citric acid, and glycolic acid, into the epidermis, dermis and other keratinous tissue.

The present invention can include other pharmaceutically acceptable components such as gelling agents, compounding agents, scents and the like. The composition of the present invention can also include other pharmaceutically active agents such as antibacterial, antifungal, antiprotozoal or antiviral agents.

This invention addresses the need for an easy-to-use topical treatment for cosmetic and therapeutic purposes of keratinous structures including the skin, nails, and hair of humans and animals, and also for the treatment of the nails, hair, hooves, and horns of animals.

Accordingly, it is an object of the invention to provide a composition and method for treating skin of humans and animals, especially dry and cracked skin, to increase the moisture of the skin.

It is another object of the invention to provide a composition and method for treating skin of humans and animals to decrease the wrinkled appearance of the skin.

Still another object of the invention is to provide a composition and method for treating skin to rejuvenate the skin and decrease the aged appearance of the skin.

It is another object of the invention to provide a method for topically applying an improved composition to animal or human keratinous tissue for enhancing the penetration of pharmacologically active substances into keratinous tissue, especially the epidermis and dermis of the skin, without damaging the tissue or causing adverse systemic effects.

Another object of the invention is to provide a composition and method for treating psoriasis.

Yet another object of the invention is to provide a composition and method for treating eczema and ichthyosis.

Still another object of the invention is to provide a composition and method for treating windburn, chapped lips, sunburn, and skin dehyrated due to exposure to chemicals.

Another object of the invention is to provide a composition and method for treating cracked fingernails and toenails of humans and animals.

Still another object of the invention is to provide a composition and method for treating cracked hooves and horns of animals.

Yet another object of the invention is to provide a composition and method for treating the cracked teats of animals and humans to prevent mastitis.

Another object of the invention is to provide a composition and method for treating dry and thinning hair of humans and animals.

Still another object of the invention is to provide a composition and method for treating calluses, corns, and any other skin conditions involving drying of the skin.

These and other objects, features and advantages of the present invention will become apparent after a review of the following detailed description of the disclosed embodiments and the appended claims.

DETAILED DESCRIPTION OF THE INVENTION

The present invention is a method of moisturizing keratinous tissue of a human or animal comprising the step of topically applying to the keratinous tissue of the human or animal, a composition comprising lecithin, in an organic solvent and water whereby the composition is delivered into the stratum corneum, epidermis and dermis. Another embodiment of the present invention comprises a method of treating keratinous tissue of a human or animal comprising the step of topically applying to the keratinous tissue of the human or animal, a composition comprising water dispersible lecithin. The present invention can optionally contain a poloxamer with the desired poloxamer being poloxamer 407.

A preferred phospholipid for use in the present invention is phosphatidylcholine, also known as lecithin. Stedman's medical dictionary [21st ed., page 879] defines lecithin as any of a group of phospholipids which upon hydrolysis yield two fatty acid molecules and a molecule each of glycerophosphoric acid and choline. There are several varieties of lecithin. Lecithin is a mixture of the diglycerides of stearic, palmitic, and oleic acids, and palmitoleic, linoleic, linolenic, and arachidonic acids, linked to the choline ester of phosphoric acid. Soybean lecithin is a preferred lecithin and may contain the following acids; palmitic, stearic, palmitoleic, oleic, linoleic, linolenic and arachidonic. In some lecithins both fatty acids are saturated while others contain only unsaturated fatty acids for example, oleic, linoleic or arachidonic. In other lecithins one fatty acid is saturated, the other unsaturated. Lecithins are found in nervous tissue, hepatic tissue, cardiac tissue, in egg yolks and in soy which constitutes the most common and economical source of phosphatidylcholine. It is therefore to be understood that any reference herein to lecithin or phosphatidylcholine is intended to include any combination of lecithin-like phospholipid compounds as is well known in the art. Examples of other phospholipids which can be used in accordance with the present invention include phosphatidylethanolamine, phosphatidylserine, phosphatidylinositol, and phosphatidic acid. A mixture of any of the above phospholipids may be also be used in the present invention. Mixtures of these phospholipids are present in natural soy lecithins.

Lecithin is described as a hygroscopic waxy solid which only forms an emulsion after dissolution with an organic solvent. The phosphatidylcholine (PC) may be characterized as amphiphilic because a polar head group is hydrophilic and has two lipophilic carbon tails. This amphiphilic property permits the surface polar heads in the aqueous phase to contract, assuming the shape of sphere. Lecithin emulsions are aggregates of micelles in water and inherently have poor stability. Williman et al., Journal of Pharmaceutical Sciences 81:871–874 (1992), found that PC, with a minimum purity of 95%, formed giant spaghetti-like micellar gels after it was dissolved in an appropriate nontoxic organic solvent. This structure is called a lecithin organogel and is thought to have a linear rather than the usual spherical structure. While not wanting to be bound by the following statement, it may be reasonable to assume the water molecules at the polar head of the PC promote additional cohesion by hydrogen bonding and thereby promote gel formation. Soy lecithin containing less than 95% PC will not gel. PC of 95% purity is expensive and what is needed is a composition and method which is cost-effective as well as safe for daily use.

The term "PLURONIC" refers to poloxamer compounds and are sold collectively under the trademark PLURONIC (BASF, Parsippany, N.J.). PLURONIC F-127 (PL 127) corresponds to poloxamer 407, a polyoxypropylene-polyoxyethylene block copolymer described by Schmolka in the *Journal of Biomedical Materials Research* 6:571–582, 1972. Other PLURONICS may be used in the present invention. As used in this application, the terms PLURONIC organogel, poloxamer organogel, and polyoxyethylene/polyoxypropylene organogel are synonymous.

The term "moisturize" or derivatives thereof, relates to the conservation or enhancement of the water content of the keratinous tissue of animals and humans, with particular reference to the skin, hair, nails, hooves and horns.

"Topical" application is used to mean local administration of the composition and its various embodiments, for example, in the treatment of dry skin.

The term "pharmacologically active agent" relates to any chemical material or compound suitable for topical administration which includes any desired local effect on animal or human tissue contacted therewith.

The term "pharmaceutically effective carrier" is used herein to mean any liquid, gel, salve, solvent, liquid, diluent, fluid ointment base, liposome, micelle, giant micelle, and the like, which is suitable for use in contact with living animal or human tissue without causing adverse physiological responses, and which does not interact with the other components of the composition in a deleterious manner.

By the term "therapeutically effective amount" of a molecule, drug or pharmacologically active agent is meant a nontoxic but sufficient amount to provide the desired therapeutic effect.

The "enhanced penetration" caused by compositions of this invention as used in topical application with this method, means increased penetration into the skin, and is achieved with compounds such as lecithin organogel, poloxamer organogel, phospholipid gels or poloxamer phospholipid gels including but not limited to phosphatidylethanolamine, phosphatidylserine, phosphatidylinositol, and phosphatidic acid and phosphatidylcholine optionally combined with n-decylmethyl sulfoxide (NDMS), PLURONIC F127, ethoxy diglycol, ethanol, or cholesterol. Enhanced penetration can be observed in many ways known to those skilled in the art.

The term "keratinous tissue" as used herein, means skin, fingernails, toenails, hooves, horns and hair, and any other cells containing keratin. The present invention provides a method and composition for topically treating damaged or diseased keratinous tissue resulting from any number of causes including, but not limited to: aging; chemical drying; radiation; burns from wind, sun, fire, cold, frostbite, radiation or chemicals; and dehydration resulting from skin disease, abrasion, sun, chemicals, wind, cold, fire, renal disease, colonic disease, hemorrhage, vasopressin imbalances, hypothalamic dysfunction, neurohypophyseal dysfunction, or other endocrine abnormalities.

The present invention includes a composition for topical treatment of keratinous tissue comprising the following components; lecithin, isopropyl palmitate and water. The combination of lecithin, isopropyl palmitate, and water is called lecithin organogel. The present invention optionally includes lecithin organogel in combination with an approximately 20% solution of PLURONIC F-127 (BASF, Parsippany, N.J.), otherwise known as poloxamer 407, in a ratio of approximately 1:4. Other PLURONICS may be used in the present invention. It is to be understood that the soy lecithin of the present invention is a preferred lecithin source and may be dissolved in isopropyl palmitate to achieve a final concentration in the composition of from approximately 20%–90%, with a more preferred final concentration of from approximately 20%–40%. Lecithins may optionally be derived from eggs, and organs such as heart, brain and liver, and used at concentrations of approximately 20%–99%, with more preferred final concentrations of from approximately 20%–40%. The composition according to the present invention can be in the form of lotions, salves, creams, ointments, liposomes, sprays, or gels. The desired form is lotions, ointments, micelles, giant micelles, and salves. Liposomes are described in detail by Oleniacz in U.S. Pat. No. 3,957,971, the entirety of which is hereby incorporated by reference.

Solvents used in the preparation of a variety of gels, including lecithin gels, all of which are appropriate in practicing the present invention, are described in Scartazzini, et al. *Journal of Physical Chemistry* 92:829–833, 1988, and Luisi, P. L. et al. *Colloid and Polymer Science* 268:356–374, 1990, both of which are incorporated herein by reference in their entirety. Specifically these solvents include the following: ethyl laurate, butyl laurate, ethyl myristate, isopropyl myristate, isopropyl palmitate, isooctane, cyclooctane, cyclododecane, methyl cyclohexane, tert-butylcyclohexane, phenylcyclohexane, bicyclohexyl, 1,3,5-triisopropylbenzene, octylbenzene, trans-decalin, (1R)-(+)-trans-pinane, (1R)-(+)-cis-pinane, n-pentane, n-hexane, n-heptane, n-octane, n-nonane, n-decane, n-undecane, n-dodecane, n-tridecane, n-tetradecane, n-pentadecane, n-hexadecane, n-heptadecane, 2,3-dimethylbutene, 1-hexene, 1,7-octadiene, tripropyllamine, tributylamine, triisobutylamine, trioctylamine, dibutyl ether and 2-dodecen-1-yl succinic anhydride.

In addition to isopropyl palmitate and isopropyl myristate, other solvents may be used in the practice of the present invention. These solvents include, but are not limited to the following: mineral spirits, kerosene, isooctane, petroleum ether, diethyl ether, benzene, toluene, methanol, ethanol, heptanol, methyl isobutyl ketone, cyclohexanone, methylene chloride, choloroform, chlorodifluoromethane, tetrahydrofuran, oleyoleate, 2-octyldodecanol, cetyl and stearyl 2-ethylhexanoate, n-octanol, ethyl laurate, isooctane, cyclopentane, cyclohexane, and cycloheptane.

In a preferred embodiment, lecithin organogel may be made from PHOSPHOLIPON 90 (American Lecithin Co., Oxford, Conn.). In this embodiment, lecithin organogel comprises 1:1 to 1.5:5 (weight/vol) of PHOSPHOLIPON 90 to isopropyl palmitate. Water is added to form the desired gel. Other penetrating agents including, but not limited to cholesterol (2% to 100%) with a preferred range of cholesterol to PHOSPHOLIPON 90 of 3:7 to 3:10. These ingredients are combined with sufficient ethanol to solubilize the mixture. Ethanol is subsequently evaporated, leaving a complex of cholesterol:PHOSPHOLIPON 90. Alternatively, 3.5%–8% ethanol may be retained in the complex to enhance penetration.

NDMS (PCAA Kinghurst, Houston, Tex.) is optionally present in the composition of the present invention at a concentration of between approximately 0.1% and 1% by weight, with a preferred concentration of between approximately 0.15% and 0.8% by weight, with the most preferred concentration of approximately 0.5% by weight. NDMS is dissolved in 10 mL of a 75% solution of ethanol. Finally, purified water is added. Ethanol (98%) may also be used to dissolve lecithin and then either boiled off completely or partially to leave a final ethanol concentration of 3% to 8.5%. While not wanting to be bound by the following statement, it is believed that 3% to 8.5% ethanol may enhance penetration.

Another preferred penetrating agent and delivery vehicle is lecithin organogel which is a combination of lecithin, isopropyl palmitate, or isopropyl myristate and water. Lecithin organogels have been described as vehicles that are useful in facilitating the delivery of low molecular weight compounds transdermally (Williman, H., et al., "Lecithin Organogel as Matrix for Transdermal Transport of Drugs", J. Pharm. Sci., Vol. 81, 1992, which is incorporated herein by reference). The lecithin organogels are obtained by adding small amounts of water to a solution of lecithin in organic solvents. Generally, lecithin organogels are prepared at room temperature by first dissolving lecithin in an organic solvent such as isopropyl palmitate or isopropyl myristate and then adding enough water while stirring to obtain the desired gel. Lecithin used in the gel preparations of the present invention generally contain at least 95% phosphatidylcholine.

The method and composition for the delivery of molecules through the skin for remoisturization and rejuvenation utilizes isopropyl myristate (IPM), isopropyl palmitate (IPP), and/or ethanol to dissolve lecithin which is necessary to form an emulsion. However, IPP and IPM can be irritating to sensitive facial skin and may produce comedowns. The invention discloses a method and composition which eliminates these risks. Ethanol is an excellent solvent as well as penetration enhancer. Ethanol may be used to dissolve the lecithin in the lipid phase. Next the ethanol is evaporated at 80° C. The aqueous phase, containing the PLURONIC, and lipid phase are heated to 60° C. and mixed together while stirring to make a PLURONIC organogel.

A water dispersible lecithin such as number 8210 or 8140 from Central Soya (Fort Wayne, Ind.) is added to an appropriate amount of deionized water containing the other components of the aqueous phase which is heated to 80° C. (heat labile ingredients may be added at the appropriate temperature during cooling). The lipid phase is heated to 80° C. and then added to the aqueous phase. Cooling with mechanical stirring produces a creamy gel without the use of solvents, such as organic solvents, which may be irritating to the skin, such as facial skin. Example 9 presents a method of making and using the water soluble gel to improve the condition of chapped hands.

Although not wanting to be bound by the following hypothesis, it is believed that the method and composition of the present invention cause an increase the water content of the skin, perhaps by increasing the fluid content of the epidermis and dermis. It is believed that the composition of the invention enhances diffusion of moisturizers, surfactants, and emollients into and possibly through the epidermal and dermal layers of the skin. It is understood that the present invention also encompasses a method and composition for delivery of molecules into the skin. These molecules optionally include, but are not limited to, elastin, elastin fragments, elastin-glycolic acid, collagen, collagen fragments, yeast extracts (skin respiratory factor), glucosamine, glucosamine sulfate, hyaluronic acid, hyaluronate, chondroitin sulfate, cholic acid, deoxycholic acid, ginseng extract, aloe vera powder, aloe vera oil, RNA and DNA fragments, ascorbyl palmitate, ascorbic acid, retinal palmitate, 7-dehydroxycholesterol, vitamin E tocopherol, vitamin E lineolate, panthenyl ethyl ester, glycerol ceramides, glycogen, DL-pyroglutamic acid, urea, sodium lactate, lactate, glycerin, sorbitol, oils of borage, evening primrose, black currant, almond and cannola, vanishing cream (polyaxyl 40 stearate, stearic acid, cetyl alcohol and stearyl alcohol), cholesterol, flavenoids (rutin, quercitin, hesperetin, hesperidenn diosmin and noringen), witch hazel (Hamamelis virginia), camomile (matri-caria Camomilla linne), parsley (Petioselinum crispum), hibiscus (Hibiscus sabdariffalinne), capric and caprylic triglycerides, amino acids (serine, lysine, glycine, alanine, arginine, aspartic acid, glutamic acid, hydroxyproline, proline, cysteine), allantoin, sodium, calcium, potassium, phosphate, and chloride, sodium lactate), alpha hydroxy acids (lactic, glycolic, citric, malonic and ammonium lactate), cocoa butter, coconut oil, jojoba oil, safflower oil, wheat germ oil, sesame oil, selachyl alcohol, shark oil, cerebrosides, proanthocyanidin, farnestol, candelellila and carnuba wax, vitamin E nicotinate, manganese ascorbate, zinc, oleyl alcohol and polysorbate 80, spermaceti, glycerol monostearate, beeswax, silicone oil, paraffin wax, ozokerit E, PEG 75 lanolin. N-decylmethyl sulfoxide is optionally included in the composition in a final concentration range of from 0.01% to 1% with a preferred range of 0.1% to 0.5%.

By allowing the passage of collagen fragments and elastin, for example, into the skin, the present invention increases the water content in the dermis also contributing to the visco-elasticity which decreases the appearance of wrinkles. Glucosamine or glucosamine sulfate stimulates dermal collagen synthesis as well as glycosaminoglycans in the epidermis which are deliquescent. This further contributes to a decreased appearance of wrinkles and to a more youthful and healthy skin.

A gelling agent optionally may be added to the formulation. Gelling agents that are suitable for use in the present invention include, but are not limited to, cellulose ethers, alginates, polyacrylates, bentonite, gelatin, tragacanth, carbomer 940, polyvinylpyrrolidone, polyvinyl alcohol, and polyoxyethylene/polyoxypropylene block copolymers, some of which are known as poloxamers. The poloxamer compounds are sold collectively under the trademark PLURONIC (BASF, Parsippany, N.J.). PLURONIC F-127 corresponds to poloxamer 407. Other PLURONICS may be used in the present invention.

Optionally, a preservative, such as benzyl alcohol, EDTA, vitamin E tocopherol, ascorbyl palmitate, ascorbic acid, alpha lipoic acid or sorbic acid, can be added to the composition. Other preservatives well known to those of ordinary skill in the art can be used in the composition.

Agents for improving the aroma of the formulation can optionally be added to the composition. A desired aroma improving agent is honey almond oil (PCAA, Kinghurst, Houston, Tex.). Other aroma improving agents include, but are not limited to, avocado oil, sesame oil, castor oil, olive oil, grapeseed oil, clove oil, groundnut oil, corn oil, lemon oil, coconut oil, lime oil, hazelnut oil, jojoba oil, carthamus oil and wheatgerm oil. The oils can be added individually or in combination. It is to be understood that various fragrances and assorted floral scents may be optionally added to the composition and are commercially available (PCAA, Houston, Tex.). Stabilizers, antioxidants, preservatives, humectants, regreasing agents, solvents or auxiliaries can be added to improve stability and/or adhesiveness of the formulations.

In addition, antimicrobial agents can be optionally added to the composition of the present invention if required. Addition of an antimicrobial agent is desirable when treating inflammatory conditions associated with acne, psoriasis or eczema.

The composition of the present invention can be administered topically either once daily or several times per day depending upon the nature and severity of the condition being treated.

It will be appreciated that other embodiments and uses will be apparent to those skilled in the art and that the invention is not limited to these specific illustrative examples.

EXAMPLE 1
Lecithin Organogel Composition Prepared With Pluronic

A preferred composition was prepared as described below. The lecithin organogel was prepared by dissolving 20 g of soy lecithin granules (PCAA, Houston, Tex.) in 20 ml of isopropyl palmitate (PCAA, Houston, Tex.). The mixture was stirred periodically for 24 hours until the soy lecithin granules were dissolved. The PLURONIC gel 20% stock solution was prepared by dissolving 16 g of PLURONIC F127 powder (BASF, Parsippany, N.J.), also called poloxamer 407, in 80 ml of purified water. Potassium sorbate (160 mg; PCAA, Houston, Tex.) was added to the PLURONIC gel 20% stock solution as a preservative. This was placed in the refrigerator at about 4° C. for about 24 hours and stirred periodically.

The composition was prepared by mixing 20 ml of the lecithin organogel with 2 ml of the honey almond oil (PCAA, Houston, Tex.) until a smooth mixture was prepared. Honey almond oil was added for fragrance. Next, 80 ml of the PLURONIC gel 20% stock solution was mixed in until a gel formed. A blender was used for this mixing step at room temperature with disinfected equipment. The gel was stored at room temperature.

EXAMPLE 2
Lecithin Organogel Composition Prepared Without Pluronic

In another embodiment of the present invention, the composition described in Example 1 was prepared using lecithin organogel without the addition of the PLURONIC gel 20% stock solution. The final concentration of lecithin organogel was in the range of 20–40% by modifying the ratio of lecithin organogel to water.

EXAMPLE 3
Hand Treatment of Human Subjects

The lecithin organogel composition (not including PLURONIC) was topically applied in cream form to the skin of one hand of each of 10 human volunteers (9–65 years of age) with a history of dry skin (xerosis) consisting of chapped hands while the other hand received treatment with control creams. These control creams labeled "A", consisted of three commercial hand creams. Another portion of each "A" cream was removed and mixed with lecithin organogel in a 1:1 ratio to create the experimental cream labeled "B". The study was done in a "blind" manner, volunteers chose either the "A" or "B" cream and were unaware whether they used control or experimental cream. Treatment continued for 7 days. Repeated application of the cream after washing and before bedtime was stressed to the participants. After 3 additional days, the volunteers applied the other cream for 7 days. The skin was subjectively evaluated for softness and feel. All 10 subjects reported superior results in promoting healing and moisturizing the skin. The treated skin appeared smoother, softer and younger and many cracks disappeared. In addition, 2 of the volunteers were afflicted with eczema which was asymptomatic after treatment with the experimental cream.

EXAMPLE 4
Application of Composition to the Human Face

A 46 year old woman exhibited wrinkling of the periorbital skin at the lateral margin of the orbit. The composition was applied topically to this region 2 to 3 times per day. Within 10 days the wrinkled appearance of the skin was dramatically diminished. This skin appeared fuller and smoother. The wrinkling of the skin was greatly reduced with fine lines generally less evident

EXAMPLE 5
Application of the Composition to the Skin Adjacent to Fingernails and Toenails Several human volunteer subjects exhibited dry and cracked skin at the bases of the fingernails and in the skin at the distal tips of the fingernails. They applied the cream for 3 to 4 times daily for 3 to 7 days and within 72 hours observed a reduction in the cracked appearance of the skin. Cracks that had developed into deep grooves began to gradually close. Within 7 days, most of these cracks had completely disappeared and pain was greatly abated.

EXAMPLE 6
Treatment of Hair

The fur of rats was shaved and various treatments applied, including lecithin organogel with PLURONIC, lecithin organogel with N-decylmethyl sulfoxide and alpha hydroxyacids (glycolic or lactic acids partially neutralized with sodium hydroxide), urea and salicylic acid. The results showed a qualitative increase in the hair shaft diameter. In addition, regrowth of the hair was faster after treatment with lecithin organogel containing PLURONIC.

In vitro treatment of hair with alpha hydroxyacids, N-decylmethyl sulfoxide, salicylic acid and urea increased hair shaft diameter by about 20% when examined with a micrometer under a microscope.

One embodiment of this application to hair is to use alpha hydroxy compounds which have a low pH (about 1.2), adjust the pH to a value of about 5–5.5 with a base such as sodium hydroxide, and apply a 20–25% concentration to the hair overnight. The hair would be washed the next morning, thereby enhancing absorption of water into the hair. The result would be thicker and more luxurious hair.

EXAMPLE 7
Preparation of Lecithin Organogel

Approximately 95% pure lecithin may be dissolved in isopropyl palmitate or isopropyl myristate on a weight basis of 1 g of lecithin per about 0.5 to 1.5 g of isopropyl palmitate or isopropyl myristate. The preferred ratio of lecithin to these solvents is about 1 g to about 0.75 g to 1 g. Next ethanol (98%) may be added while stirring at 80° C. until the alcohol is boiled off. Water is then added with stirring at approximately 20 to 40% with a preferred concentration of about 30%.

EXAMPLE 8
Lecithin Organogel Prepared with PLURONIC

A penetration enhancer of the present invention is PLURONIC F-127 (BASF, Parsippany, N.J.) which permits use of lecithins of lesser purity than those required in formation of lecithin organogels as taught by Williman et al. PLURONIC F-127 is employed at concentrations of about 0.1% to 45% in a ratio PLURONIC to lecithin of about 1:0.5 to 1:6.0. A preferred final concentration of PLURONIC F-127 is 5% to 20% in a ratio of PLURONIC to lecithin of 1:2 to 1:4. Lecithins of concentrations of approximately 5% to 90% are first dissolved in isopropyl palmitate, isopropyl myristate and/or 98% ethanol. The addition of four parts of PLURONIC F-127 (20% solution) to the dissolved lecithin produces a cost effective gel. In addition, water, carboxyethyl cellulose, carboxymethyl cellulose, other PLURONICS, and other agents known to one skilled in the art may be used. These mixtures are known PLURONIC organogels or poloxamer organogels.

EXAMPLE 9
Water Dispersible Lecithin without Organic Solvent

Nurses, aids and other personnel must wash their hands after degloving which may be as frequent as 40–80 times in an 8–10 hour shift. Three nurses at an intensive care unit at a local hospital had a chronic problem with chapping and were stressed by the possibility of HIV or Step A infection. All previous products, whether purchased over the counter or by prescription, had not successfully treated the chapping. The gel was prepared as follows. Excellent results were evident in 3–5 days.

| Part 1 | |
|---|---|
| Lecithin 8120 | 7.5% |
| Deionized water | 15% |
| DL-pyroglutamic acid | 5% |
| Urea | 2% |
| Glucosamine/glucosamine sulfate | 2% |
| Manganese ascorbate | 0.5% |
| PL127 20% | 14% |
| Panthenyl ethyl ester | 1% |

| Part 2 | |
|---|---|
| Glycerol | 5% |
| Aloe vera oil | 3% |
| Almond oil | 2% |
| Vanishing cream (stearyl alcohol, steric acid, Polyaxyl 40 stearate) | 8.5 g |
| Squalene | 2% |

| Part 3 | |
|---|---|
| Retinal palmitate | 10,000 units/gm: 1% |
| 7 dehydrocholesterol | 1,000 units/gm 0.1% |
| Ascorby palmitate | 2 ml 2% |
| Vitamin E tocopherol | 1 ml 1% |
| Proanthocyanidin | 1 ml 1% |

Procedure

Part 1 was heated to 70° C. with stirring. Part 2 was heated to 75° C. with stirring. Parts 1 and 2 were combined with stirring. Part 3 was added to the batch at 35° C. with stirring.

EXAMPLE 10
Lecithin Dissolved in Ethanol which is then Evaporated

| Part 1 | |
|---|---|
| Deionized water | 38.5% |
| PL127 20% | 13% |
| Glucosamine/glucosamine sulfate | 2% |
| Allantoin | 1% |
| Ammonium lactate | 5% |
| dl-pyroglutamic acid | 2% |

| Part 2 | |
|---|---|
| Vanishing cream | 7% |
| Cholesterol | 5% |
| Aloe vera oil | 5% |
| Glycerol | 5% |
| Safflower oil | 2% |
| Borage oil | 2% |
| Phospholipon 90H | 7.5% |
| ethanol | 20 ml |

| Part 3 | |
|---|---|
| Retinal palmitate | 1% |
| 7 dehydrocholesterol | 1% |
| Ascorbyl palmitate | 2% |
| Vitamin E tocopherol | 1% |
| Proanthocyanidin | 1% |

Procedure

Part 1 was heated to 60° C. while stirring, thereby dissolving the lecithin and evaporating the ethanol. Ethanol was added to Part 2 at 80° C. while stirring. After the ethanol evaporated, part 2 was added to part 1 while stirring mechanically. This mixture was stirred until a gel formed at about 60° C. Fragrance was optionally added with part 3 at 35° C. to the batch while mechanically stirring.

This composition was applied to the skin of a 54 year old male and also to the skin of four females of 49, 20, 12, and 11 years of age. Each of these subjects complained of dry skin prior to application of the composition. Following topical application of the composition, each subject exhibited superior moisturization of the skin in the treated area.

This composition is an elegant and efficacious moisturizer which has no irritating solvent and may be used on the faces of children, as well as adults, with sensitive skin.

EXAMPLE 11
Comparison of Lecithin Dissolved in Isopropyl Palmitate or Isopropyl Myristate with and without PLURONIC

| Part 1 Composition 1 | | Part 1 Composition 2 | |
|---|---|---|---|
| Deionized water | 53% | PL127 20% | 53% |
| Ammonium lactate | 5% | Ammonium lactate | 5% |
| Citric acid | 5% | Citric acid | 5% |

| Part 2 Composition 1 | | Part 2 Composition 2 | |
|---|---|---|---|
| Lecithin granules dissolved in IPM or IPP | 30% | Lecithin granules dissolved in IPM or IPP | 30% |
| | | Glycerol | 5% |
| Glycerol | 5% | Capric/caprylic triglycerides | 2% |
| Capric/caprylic triglycerides | 2% | | |

Procedure for making Composition 1

An equal weight of IPM was dissolved with lecithin granules and allowed to stand overnight. Addition of part 2 to part 1 produced a 2-phase system which did not disperse with mixing at 60° C.

Procedure for making Composition 2

Part 1 was heated to 60° C. Part 2 was heated to 60° and added to part 1 with mechanical mixing. The mixture was allowed to cool.

A similar area on either arm was chosen to test the efficacy of the two compositions which were applied three times a day for five minutes and then washed off with soap. The moisture content of the outer stratum corneum may be evaluated subjectively in that a rough, flaky appearance is obvious and a white dust like material is evident upon scratching lightly with a finger tip. These impressions are clinically valuable, but very difficult to quantify.

D-Squame discs (CuDerm Corp., Dallas Tex.) were used to quantify dry skin and objectively evaluate relative efficacy of moisturizers. The disc is applied firmly to a similar area of each arm, pressed firmly, and then transferred to a black card for evaluation. Normal skin produces a few areas of small clumps of cells or even a fine even single layer. Very dry skin produces heavy amounts of scaling.

In order to simulate the work conditions which cause chapping the compositions were removed 15 minutes after application by washing with soap and water.

After 24 hours the PLO moisturizer was rated 3 on a 1–5 scale, with 5 being the heaviest clumping. Composition 1 was a 4–5 and remained such for 5 days. Over the course of the next 4 days, the PLO composition produced less scaling 2–5 and was softer to the touch. The finger tip could not produce the white powder as was possible before the trial.

The production of the PLO allowed an effective delivery of the active ingredients which produced the moisturization. Lower grade lecithin dissolved in an organic solvent has poor moisturizing properties.

It should be understood, of course, that the foregoing relates only to preferred embodiments of the present invention and that numerous modifications or alterations may be made therein without departing from the spirit and scope of the invention.

What is claimed is:

1. A method of treating keratinous tissue of a human or animal comprising the step of topically applying to the keratinous tissue a composition comprising lecithin, poloxamer 407, a solvent and water.

2. The method of claim 1, wherein the solvent is isopropyl palmitate, isopropyl myristate, ethyl myristate, 2-octyldodecanol or ethanol.

3. The method of claim 1, further comprising compositions selected from the group consisting of antimicrobial, antibacterial, antifungal, antiprotozoal, and antiviral agents.

4. The method of claim 1, further comprising glucosamine or glucosamine sulfate.

5. The method of claim 1, further comprising molecules selected from the group consisting of alpha hydroxy compounds, glycolic acid, citric acid, and lactic acid.

6. The method of claim 1, further comprising molecules selected from the group consisting of glycerol, urea, ceramides, squalene, elastin, salicylic acid, dimethicone, lanolin, chondroitin sulfate, hyaluronic acid, collagen, and collagen fragments.

7. The method of claim 1, in the form selected from the group consisting of lotions, salves, creams, liposomes, sprays, micelles, and gels.

8. A method of treating psoriasis comprising the step of topically applying to the skin of a human or animal the composition of claim 1.

9. A method of treating eczema comprising the step of topically applying to the skin of a human or animal the composition of claim 1.

10. A method of treating ichthyosis comprising the step of topically applying to the skin of a human or animal the composition of claim 1.

11. The method of claim 1, further comprising molecules selected from the group consisting of elastin, elastin fragments, elastin-glycolic acid, collagen, collagen fragments, yeast extracts, skin respiratory factor, glucosamine, glucosamine sulfate, hyaluronic acid, hyaluronate, chondroitin sulfate, cholic acid, deoxycholic acid, ginseng extract, aloe vera powder, aloe vera oil, RNA and DNA fragments, ascorbyl palmitate, ascorbic acid, retinal palmitate, 7-dehydroxycholesterol, vitamin E tocopherol, vitamin E lineolate, panthenyl ethyl ester, glycerol ceramides, glycogen, DL-pyroglutamic acid, urea, sodium lactate, lactate, glycerin, sorbitol, oils of borage, evening primrose, black currant, almond and canola, vanishing cream, cholesterol, flavenoids, witch hazel, chamomile, parsley, hibiscus, capric and caprylic triglycerides, amino acids, allantoin, sodium, calcium, potassium, phosphate, chloride, sodium lactate, alpha hydroxy acids, cocoa butter, coconut oil, jojoba oil, safflower oil, wheat germ oil, sesame oil, selachyl alcohol, shark oil, cerebrosides, proanthocyanidin, farnestol, candelellila, carnuba wax, vitamin E nicotinate, manganese ascorbate, zinc, oleyl alcohol, polysorbate 80, spermaceti, glycerol monostearate, beeswax, silicone oil, paraffin wax, ozokerit E, and PEG 75 lanolin.

12. The method of claim 1, wherein the composition further comprises a carbomer.

13. A method of treating keratinous tissue of a human or animal comprising the step of topically applying to the keratinous tissue a composition comprising water dispersible lecithin and poloxamer 407.

14. The method of claim 13, wherein the composition further comprises a carbomer.

15. The method of claim 13, further comprising compositions selected from the group consisting of antimicrobial, antibacterial, antifungal, antiprotozoal, and antiviral agents.

16. The method of claim 13, further comprising glucosamine or glucosamine sulfate.

17. The method of claim 13, further comprising molecules selected from the group consisting of alpha hydroxy compounds, glycolic acid, citric acid, and lactic acid.

18. The method of claim 13, further comprising molecules selected from the group consisting of glycerol, urea, ceramides, squalene, elastin, salicylic acid, dimethicone, lanolin, chondroitin sulfate, hyaluronic acid, collagen, and collagen fragments.

19. The method of claim 13, in the form selected from the group consisting of lotions, salves, creams, liposomes, sprays, micelles, and gels.

20. A method of treating psoriasis comprising the step of topically applying to the skin of a human or animal the composition of claim 13.

21. A method of treating eczema comprising the step of topically applying to the skin of a human or animal the composition of claim 13.

22. A method of treating ichthyosis comprising the step of topically applying to the skin of a human or animal the composition of claim 13.

23. The method of claim 13, further comprising molecules selected from the group consisting of elastin, elastin fragments, elastin-glycolic acid, collagen, collagen fragments, yeast extracts, skin respiratory factor, glucosamine, glucosamine sulfate, hyaluronic acid, hyaluronate, chondroitin sulfate, cholic acid, deoxycholic acid, ginseng extract, aloe vera powder, aloe vera oil, RNA and DNA fragments, ascorbyl palmitate, ascorbic acid, retinal palmitate, 7-dehydroxycholesterol, vitamin E tocopherol, vitamin E lineolate, panthenyl ethyl ester, glycerol ceramides, glycogen, DL-pyroglutamic acid, urea, sodium lactate, lactate, glycerin, sorbitol, oils of borage, evening primrose, black currant, almond and canola, vanishing cream, cholesterol, flavenoids, witch hazel, chamomile, parsley, hibiscus, capric and caprylic triglycerides, amino acids, allantoin, sodium, calcium, potassium, phosphate, chloride, sodium lactate, alpha hydroxy acids, cocoa butter, coconut oil, jojoba oil, safflower oil, wheat germ oil, sesame oil, selachyl alcohol, shark oil, cerebrosides, proanthocyanidin, farnestol, candelellila, carnuba wax, vitamin E nicotinate, manganese ascorbate, zinc, oleyl alcohol, polysorbate 80, spermaceti, glycerol monostearate, beeswax, silicone oil, paraffin wax, ozokerit E, and PEG 75 lanolin.

* * * * *